(12) United States Patent
Adams et al.

(10) Patent No.: US 9,750,398 B2
(45) Date of Patent: Sep. 5, 2017

(54) UNIVERSAL CAP

(75) Inventors: Christopher Steven Adams, Montgomery, TX (US); Travis Henry Bendele, Conroe, TX (US); Don Byrne, Montgomery, TX (US)

(73) Assignee: Medivators Inc., Minneapolis, MN (US)

( * ) Notice: Subject to any disclaimer, the term of this patent is extended or adjusted under 35 U.S.C. 154(b) by 7 days.

(21) Appl. No.: 13/164,766

(22) Filed: Jun. 20, 2011

(65) Prior Publication Data

US 2012/0091092 A1    Apr. 19, 2012

Related U.S. Application Data

(60) Provisional application No. 61/393,238, filed on Oct. 14, 2010.

(51) Int. Cl.
*B65D 41/04* (2006.01)
*A61B 1/015* (2006.01)
*A61B 1/00* (2006.01)

(52) U.S. Cl.
CPC .......... *A61B 1/015* (2013.01); *A61B 1/00119* (2013.01); *A61B 1/00128* (2013.01); *A61B 1/00137* (2013.01)

(58) Field of Classification Search
USPC .............. 215/329, 316, 341, 349, 350, 351; 220/705, 378, 709
See application file for complete search history.

(56) References Cited

U.S. PATENT DOCUMENTS

| | | | | |
|---|---|---|---|---|
| 2,186,908 A | * | 1/1940 | Page et al. ................. | 215/248 |
| 3,063,904 A | * | 11/1962 | Ryan ..................... | A61K 35/14 |
| | | | | 424/613 |
| 3,448,881 A | * | 6/1969 | Zipper ....................... | 215/318 |
| 3,520,436 A | * | 7/1970 | Vercillo ...................... | 215/348 |
| 3,741,423 A | * | 6/1973 | Acton et al. ................ | 215/318 |
| 3,915,336 A | * | 10/1975 | Spreng ....................... | 220/284 |
| 3,979,004 A | * | 9/1976 | Bertario ...................... | 215/341 |
| 4,076,152 A | * | 2/1978 | Mumford .................... | 222/545 |
| 4,280,631 A | * | 7/1981 | Lohrman .................... | 215/204 |
| 4,347,939 A | * | 9/1982 | Upton ........................ | 215/252 |

(Continued)

FOREIGN PATENT DOCUMENTS

| | | |
|---|---|---|
| GB | 786282 | 11/1955 |
| JP | 2006094758 | 4/2006 |
| WO | 2010/028172 A1 | 3/2010 |

OTHER PUBLICATIONS

PCT/US2011/056176, International Search Report and Written Opinion of the International Searching Authority, mailing date Jan. 20, 2012.

(Continued)

*Primary Examiner* — Jeffrey Allen
(74) *Attorney, Agent, or Firm* — Sorell, Lenna & Schmidt LLP; William D. Schmidt, Esq.

(57) ABSTRACT

A combined tube set for a disposable water bottle for an endoscope includes a cap with threads suitable for attachment to various water bottles. The combined tube set provides a first tube set for rinsing that includes an air and water tubes, air/water connector, and anchor. The combined tube set also provides a second tube set for irrigation that includes an irrigation connector, backflow valve(s), and flexible tubing section.

47 Claims, 17 Drawing Sheets

(56) References Cited

U.S. PATENT DOCUMENTS

| | | | |
|---|---|---|---|
| 4,407,422 A * | 10/1983 | Wilde et al. | 215/246 |
| 4,462,502 A * | 7/1984 | Luenser et al. | 215/329 |
| 4,487,325 A * | 12/1984 | Willingham | 215/307 |
| 4,629,083 A * | 12/1986 | Druitt | B65D 41/045 215/329 |
| 4,668,458 A * | 5/1987 | Whitney | 264/249 |
| 4,730,583 A * | 3/1988 | Stritzke | 123/188.6 |
| 4,911,315 A * | 3/1990 | Shrum | 215/229 |
| 4,934,545 A * | 6/1990 | Pezzoli et al. | 215/250 |
| 4,997,429 A * | 3/1991 | Dickerhoff et al. | 604/411 |
| 5,041,105 A * | 8/1991 | D'Alo et al. | 604/411 |
| 5,041,106 A * | 8/1991 | Noji et al. | 604/411 |
| 5,064,084 A * | 11/1991 | McBride et al. | 215/350 |
| 5,285,913 A * | 2/1994 | Morton | 215/349 |
| 5,381,924 A * | 1/1995 | Kiefel | 220/709 |
| 5,405,323 A | 4/1995 | Rogers et al. | |
| 5,437,654 A * | 8/1995 | McVay | A61M 3/0233 222/189.06 |
| 5,470,324 A | 11/1995 | Cook et al. | |
| 5,762,219 A * | 6/1998 | Parrinello | 215/351 |
| 5,782,383 A * | 7/1998 | Robinson | 222/81 |
| 5,830,128 A * | 11/1998 | Tanaka | 600/158 |
| 6,142,325 A * | 11/2000 | Chomik | 215/343 |
| 6,142,979 A | 11/2000 | McNally et al. | |
| 6,202,872 B1 * | 3/2001 | Smeyak et al. | 215/343 |
| 6,202,887 B1 * | 3/2001 | Petit | 220/849 |
| 6,210,322 B1 * | 4/2001 | Byrne | 600/158 |
| 6,264,636 B1 | 7/2001 | Holm et al. | |
| 6,309,347 B1 | 10/2001 | Takahashi et al. | |
| 6,390,315 B1 | 5/2002 | Giddings et al. | |
| 6,485,412 B1 * | 11/2002 | Byrne | 600/158 |
| 6,523,711 B1 | 2/2003 | Hughes et al. | |
| 6,544,246 B1 * | 4/2003 | Niedospial, Jr. | 604/411 |
| 6,837,400 B2 * | 1/2005 | Leoncavallo et al. | 222/189.09 |
| 7,066,902 B1 | 6/2006 | Ott et al. | |
| 7,281,639 B2 * | 10/2007 | Yoshida et al. | 220/304 |
| 7,757,872 B2 * | 7/2010 | Ver Hage | 215/229 |
| 7,926,818 B2 * | 4/2011 | Isono | 277/630 |
| 8,640,898 B2 * | 2/2014 | Parrinello | 215/341 |
| 2002/0092858 A1 * | 7/2002 | Bowman | 220/709 |
| 2003/0029876 A1 | 2/2003 | Giraud | |
| 2003/0073971 A1 * | 4/2003 | Saker | 604/403 |
| 2003/0116523 A1 * | 6/2003 | Druitt et al. | 215/341 |
| 2003/0189023 A1 * | 10/2003 | Gonzalez | 215/260 |
| 2007/0238929 A1 | 10/2007 | Aizenfeld et al. | |
| 2008/0125758 A1 | 5/2008 | Marisi | |
| 2008/0179273 A1 * | 7/2008 | Hidding | 215/216 |
| 2011/0263939 A1 * | 10/2011 | Kaye et al. | 600/158 |
| 2012/0088974 A1 | 4/2012 | Maurice | |

OTHER PUBLICATIONS

PCT/US2011/056185, International Search Report and Written Opinion of the International Searching Authority, mailing date Jan. 19, 2012.

Notification of Transmittal of the International Search Report and the Written Opinion of the International Searching Authority, or the Declaration (Oct. 24, 2011).

\* cited by examiner

UNIVERSAL CAP

The present patent application claims the benefit of a prior filed U.S. Provisional Patent Application Ser. No. 61/393,238, filed on Oct. 14, 2010.

FIELD OF THE INVENTION

This invention relates to endoscopic systems. More particularly, this invention relates to a combined tube set for insufflation, irrigation and rinsing which allows an endoscopic system to be connected to a water bottle. The present invention also relates to a cap and more particularly to a universal fit bottle cap that is capable of sealing and/or being threaded on various types of bottles; for example water bottles for endoscope systems or other medical applications.

BACKGROUND OF INVENTION

Endoscopic instruments have been developed to provide surgeons with an internal view of the organ or body passage requiring treatment. Such endoscopes typically have channels through which flexible instruments, such as a miniaturized forceps, are inserted and advanced. The endoscope assembly includes an elongated flexible cable equipped at one end with an eyepiece or other viewing means and at the other end with an imaging means. The cable transmits images or image-producing signals from the illuminated operative site to the viewing means so that the surgeon will have visual confirmation of the action of the instrument's working end. The cable also provides a flow passage for the delivery of fluid (liquid or gas) for irrigation, insufflation, rinsing, or other purposes. For instance, it may be necessary to provide the optic head with a flow of sterile water. The passage of the sterile water across the optic head prevents the buildup of materials on the imaging means. This flow of water operates, in a sense, like a windshield wiper/washer assembly.

In normal practice, the endoscopic instrument has a control body which provides several ports that allow connectors to be attached for irrigation, insufflation, rinsing, or other purposes. These ports may include a variety of fittings that are suitable for various purposes. For example, air and water ports can receive an air/water connector suitable for providing air and/or water for rinsing and other purposes. As such, the air and water are delivered through the connector into the light guide connector or control body of the endoscope. The light guide connector or the control body can also include an irrigation port so as to allow irrigation water to be directly provided to the endoscope. Suitable valves are provided on the control body so as to control the flow of water and/or air through the control body and the flexible cable of the endoscope.

Unfortunately, there is usually a great expense associated with maintaining sterility of the equipment and/or water. Sterile water can be provided for rinsing from a water bottle that is connected to the endoscopic instrument via tubing. The tubing has a fitting at one end so as to allow the tube to be connected to the air/water port of the endoscopic instrument, and the other end of the tubing is inserted into the water bottle. Typically, the fitting will include two tubes, one providing water and the other providing air. Sometimes the two tubes may be concentric with an inner tube providing water and an outer tube providing air. The inner tube extends through a cap into the water bottle, and the outer tube is connected to the cap of the water bottle. Air may be delivered through the area between the inner tube and the outer tube so as to pressurize the interior of the water container. In some embodiments, the gas that pressurizes the bottle and insufflates the lumen may be supplied through a separate tube that interfaces with the bottle cap; in such a system, the gas flows from the bottle to the endoscope through the space between the inner tube and the outer tube. This will force water to flow through the tube and into the endoscope at a desired rate. For example, inner and outer tube sets that are utilized with endoscopes are described in U.S. Pat. Nos. 6,210,322 and 6,485,412, the contents of which are hereby incorporated by reference (see, e.g., '322 patent at Col. 3, 1. 42-Col. 4, 1. 6 and '412 patent at Col. 4, 11. 34-48).

The purpose of irrigation is to clear debris from the field of view. When debris such as digestive waste, mucous, blood, and detached tissue cover portions of the lumen wall, the operator may be unable to make a proper assessment of the condition of the tissue or perform actions such as biopsy removal or cautery. When irrigation is desired, the endoscopic instrument can be connected to another water bottle using another set of tubing. One end of an irrigation tube is connected to an irrigation port of the endoscopic instrument, and the other end of the tubing extends through a cap so that it may be placed in a water bottle. The irrigation tube may provide a section of flexible tubing that is insertable into a peristaltic pump. The peristaltic pump provides water flow to the endoscope that is suitable for irrigation. The irrigation system moves water by drawing it out of the bottle with a peristaltic pump, so it requires a vent to allow air to enter the bottle. In contrast, the insufflation and lens rinsing system moves water by pushing it out of the bottle with internal pressure, so the tubing and bottle assembly must be sealed to maintain the pressure.

After usage, the two water bottles, the tubing, and the associated fittings are sterilized or disinfected if they are not disposable items. In the case that the items are disposable, two water bottles, tubing, and associated fittings are discarded. If the items are sterilized or disinfected, there is a considerable labor expense associated with cleaning, and disinfecting or autoclaving. Additionally, there is also the possibility of residual contaminants residing in the area of connection between the tubes and the bottle. This creates a considerable expense to the hospital in either case. In some systems, two bottles are required when the user desires to perform both functions because the designs of these systems treat them as separate and independent, individual systems.

Research has demonstrated that there is a clinical benefit when insufflation is performed using warm (e.g. body temperature) water instead of dry room temperature air. It is expected that this benefit is due to the fact that the warm water is more similar to the natural surroundings of the internal tissue than the cool, dry air. The sudden loss of temperature caused by insertion of air can make the muscles in the lining of the lumen contract and affect blood flow to the tissue. Also, when warm water is used for insufflation, the debris remaining on the tissue is readily washed away, which improves visibility for cancer screening when the user removes the water and adds air for insufflation. Warm water infusion typically is performed as the endoscope is inserted into the patient. The water is subsequently removed and replaced with air as the endoscope is being removed and the operator is looking for problematic tissues (such as cancerous tumors).

Just as the tissue is most commonly subjected to warm liquids than cool dry air, the gas that does pass through the digestive tract tends to be warm and humid. Thus it is advantageous to use warm, humid air whenever insufflation is performed with air. In some systems, the gas that enters the endoscope for insufflation first passes through the water bottle and then into the endoscope. In such a system, it is possible to warm the gas prior to it entering the bottle and/or warm the water in the bottle. If the gas is then forced to enter the bottle at the bottom and bubble to the top, it absorbs water and heat then leaves the bottle warm and humid as it travels to the endoscope for insufflation. A clinical benefit is expected as the gas is less likely to dry or cool the tissues, thus reducing cramping of the luminal wall. If the gas used for this procedure is carbon dioxide instead of atmospheric air, the carbon dioxide absorbs into the tissues more than 100 times faster. The absorption rate of carbon dioxide into digestive tissues is 100 to 150 times that of oxygen and nitrogen, which combine to make up about 99% of atmospheric air. Because carbon dioxide is absorbed into the tissues and expired through the respiratory system, the gas in the lumen does not have to pass through the remainder of the digestive system, thus improving patient discomfort and speeding recovery. The lens rinsing system, similar to the irrigation system, comprises a continuous liquid path interrupted only by valves. (The irrigation system fluid path also is interrupted by the pump rollers.) It is desirable to maintain sterility of the water in the water bottle that serves a source of water for lens rinsing. Thus, it is desirable to add a check valve in the lens rinsing flow path. This check valve is preferably incorporated in the air/water connector of the tube set since the valve can then be disposed of with the tube set rather than being reprocessed with the endoscope. The check valve can help to prevent crosscontamination.

SUMMARY OF THE INVENTION

It is an object of the current invention to disclose a cap with a liner inside the cap which is capable of sealing on multiple surfaces, specifically of a variety of bottles including bottles used in medical applications such as endoscopic systems for example. In an embodiment, the cap comprises a thread on an inner surface of said cap and a liner inside the cap which is capable of sealing on multiple surfaces, and a top end wherein the top end comprises at least an opening. The opening can be a hole to fit a tubing. In an embodiment, the cap and the liner are made of the same material including a plastic material, an elastomeric material, thermoplastic elastomeric material, rigid polymer, acrylonitrile butadiene styrene (ABS), methyl methacrylate acrylonitrile butadiene styrene (MABS), polyvinyl chloride (PVC), polystyrene, polycarbonate, polyproylene, nylon, silicone, rubber or combination thereof. The cap and liner can also be made of different materials. The cap and the liner can be one contiguous body. In a further embodiment of the invention, the liner comprises an inner diameter which is not constant such that it is capable of engaging a variety of bottle necks of varying heights and diameters. In an embodiment, the inner diameter decreases axially toward the top end. In a further embodiment, the thread has a first diameter and second diameter, wherein the first diameter is bigger than the second diameter. In a further embodiment, the thread is a positive thread.

Another object of the invention is a cap comprising a liner capable of sealing on multiple surfaces wherein the cap further comprises on an inner surface a thread, wherein the thread is adapted to engage a variety of bottles. In an embodiment of the invention, the thread has a trapezoid geometry comprising a first base and a second base, wherein the first base is larger than the second base and wherein the first base is adjacent to the wall of the cap. In another embodiment, the trapezoidal geometry comprises rounded corners. In an embodiment, the cap and the liner are made of the same material including a plastic material, an elastomeric material, thermoplastic elastomeric material, rigid polymer, acrylonitrile butadiene styrene (ABS), methyl methacrylate acrylonitrile butadiene styrene (MABS), polyvinyl chloride (PVC), polystyrene, polycarbonate, polypropylene, nylon, silicone, rubber or combination thereof. The cap and liner can also be made of different materials. The cap and the liner can be one contiguous body. In a further embodiment of the invention, the liner comprises a substantially L-shaped cross section and has varying inner diameters such that it is capable of engaging a variety of bottle necks of varying heights and diameters. Examples of bottles include but are not limited to sterile bottles for medical applications such as sterile water bottles. A further embodiment of the invention includes a cap comprising an air filter.

Another object of the invention is a cap comprising a top end and a bottom end, wherein the inner surface is tapered at an angle of about 2 degrees such that the diameter of the bottom end is larger than the diameter of the top end.

A further object of the invention is a cap comprising at least one gasket such that the gasket provides a seal between the bottle cap and the bottle. In one embodiment, the seal is air tight or nearly air tight.

A further object of the invention is a cap comprising a thread on an inner surface, a liner having at least two sealing surfaces at least partially above the thread, and a top end, wherein said top end comprises at least three holes. In one embodiment at least one of the holes fits an irrigation tubing. In another embodiment, at least one of the holes fits a water/air tube set. In yet another embodiment, at least one of the holes fits a tubing for insufflation.

A further object of the invention is a cap capable of sealing on multiple surfaces comprising a liner wherein the liner comprises a substantially L-shaped cross sectional profile and having at least two diameters. In one embodiment the cap has a thread on an inner surface, wherein the thread is adapted for engaging a variety of bottles and the cap has a top end wherein the top end comprises at least one hole to fit a tubing. A further object of the invention is a cap comprising an inner surface having positive threads, wherein the threads are adapted for engaging a variety of sterile water containers; a top end comprising at least one opening; said opening having a flexible tubing disposed therein.

A further object of the invention is a liner that is capable of sealing on a variety of caps. One embodiment of the liner comprises a substantially L-shaped cross-sectional profile comprising various diameters. The liner can be made of thermoplastic elastomeric material, MABS, ABS, polypropylene, polyvinyl chloride, nylon, silicone, rubber or combinations thereof. A further objective of the current invention is to provide a cap comprising a liner capable of sealing on multiple surfaces, wherein the cap comprises at least one hole to fit a tubing and wherein liner seals the area between the cap and the tubing.

A further object of the invention is a cap for sealing a sterile water bottle comprising: a thread on an inner surface providing less than 720° of thread engagement with said sterile water bottle; and at least two sealing surfaces above said thread.

A further object of the invention is a cap comprising: a liner capable of sealing on multiple surfaces; a thread on an inner surface; a top end; wherein the top end comprises at least one hole fit for a tubing wherein the liner seals the area between the cap and the tubing.

DETAILED DESCRIPTION

Figure 1:
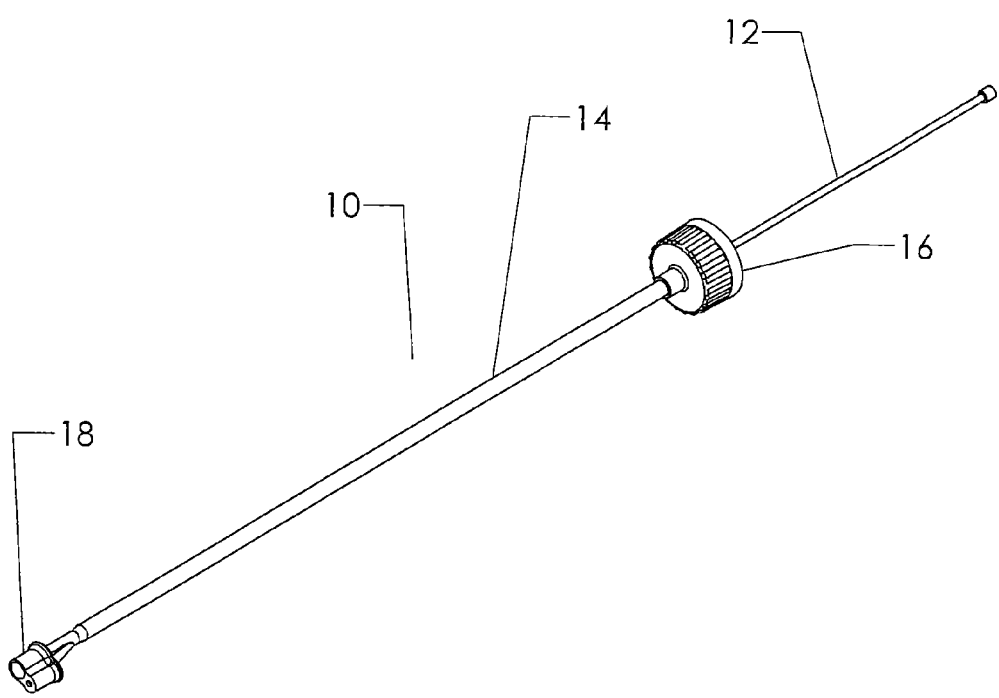
FIG. 1 is an illustrative embodiment of an air/water tube set.

Refer now to the drawings wherein depicted elements are not necessarily shown to scale and wherein like or similar elements are designated by the same reference numeral through the several views.

FIG. 1 shows an example of a system for connecting a water bottle to an endoscope for lens rinsing or an air/water tube set 10. Tube set 10 includes water tube 12 and air tube 14. While water tube 12 extends through air tube 14 in the example shown, it should be noted that in other embodiments the water and air tubes may be separated or the water tube may not extend through the air tube. Tube set 10 provides a connector 18 on one end of the tube set that can be connected to an endoscope (not shown). Cap 16 is connected to the air tube 14 and water tube 12 extends through cap 16.

Figure 2:
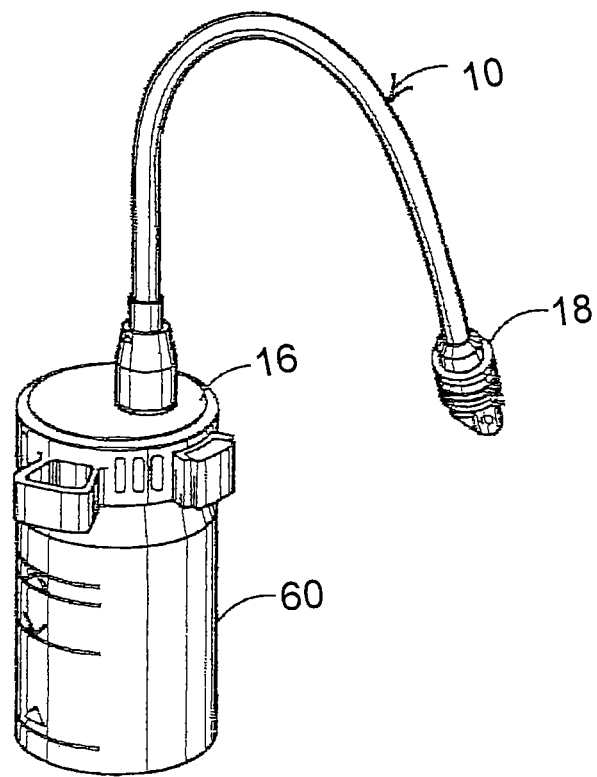
FIG. 2 is an illustrative embodiment of an air/water tube set secured to a water bottle.

FIG. 2 shows an example of an air/water tube set 10 attached to water bottle 60. When cap 16 is placed on a water bottle, water tube 12 extends into the water bottle to provide a source of water for the endoscope. Connector 18 (shown as an Olympus connector in contrast to FIG. 1) may be connected to ports on the endoscope to provide water for lens rinsing.

Figure 3:
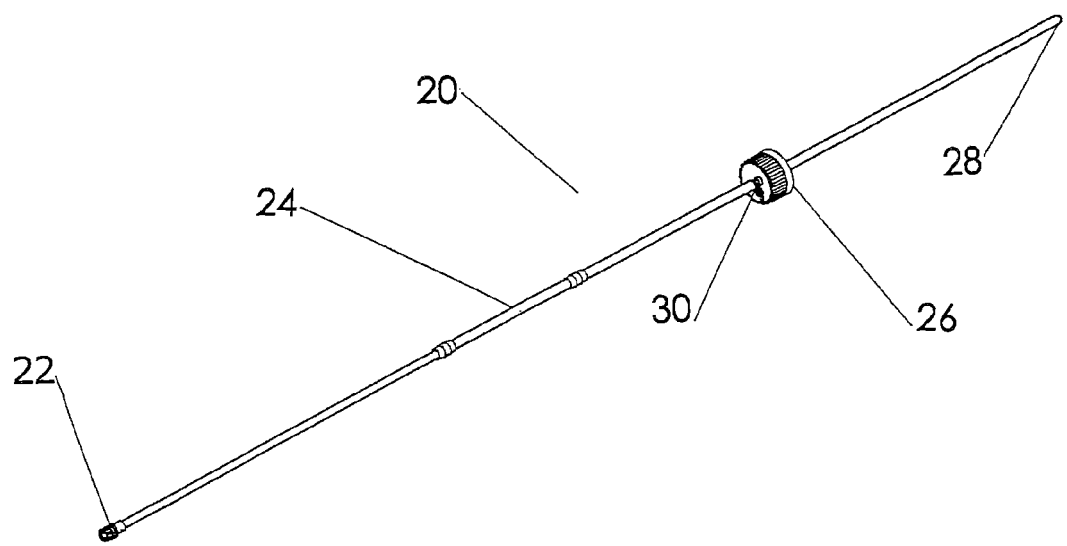
FIG. 3 is an illustrative embodiment of an irrigation tube set.

FIG. 3 shows an example of a system for connecting a water bottle to an endoscope for irrigation or an irrigation tube set 20. One end of the irrigation tube set 20 has a connector 22 that can be mated to an endoscope. Irrigation tube set 20 may include flexible section 24 of tubing that can be inserted into a peristaltic pump, which pumps the water to the endoscope for irrigation. Irrigation tube set 20 is attached to cap 26 and the water bottle end 28 of the irrigation tube set 20 passes through the cap so that it may extend into a water bottle when the cap is placed on the water bottle. While the irrigation tube set 20 is formed from three separate pieces of joined tubing as described, in other embodiments, irrigation tube 20 may be formed from fewer or more joined tubes. Cap 26 provides vent 30. Since the pump is drawing water through the tubing, an equivalent volume of air must be allowed to enter the bottle. In the embodiment shown, the air is filtered, whereas in some embodiments the air is not filtered, so it may enter by some other gap in the system.

Figure 4:
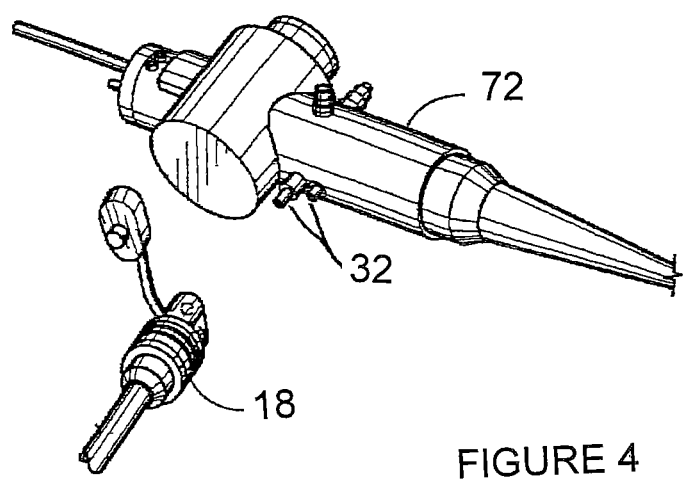
FIG. 4 is an illustrative embodiment of an endoscope.

FIG. 4 shows an example of endoscope 72 light guide connector with several ports, such as air/water ports 32 and irrigation port (not shown). Connector 18 for air/water tube set 10 connects to air/water ports 32 of endoscope 72. Connector 22 for irrigation tube set 20 connects to irrigation port (not shown) of endoscope 72. When connectors 18, 22 are connected to endoscope 72 water for lens rinsing or irrigation can be provided to the endoscope.

Air/water tube set 10 and irrigation tube set 20 require two separate water bottles for use with endoscope 72. If the tube sets and water bottles are reusable, great expense is associated with maintaining sterility of the equipment and/or water. There is a considerable labor expense associated with manual or automated cleaning, and disinfection or autoclaving the equipment. Additionally, there is also the possibility of residual contaminants remaining in the area of connection between the tubes and the bottle. Further, because air/water tube set 10 and irrigation tube set 20 each require their own water bottle more equipment must be sterilized, or disposed of if not reusable, after the equipment has been used.

Additionally various types of water bottles and water containers exist for endo scope systems. Presently, disposable water bottles are manufactured in 250 milliliter, 500 milliliter and 1,000 milliliter sizes. These water bottles have slightly varying diameter necks of slightly varying lengths. The thread structure on the neck of each of these water bottles is slightly different. The difference in length of neck and configuration of threads is the result of water bottles being manufactured by several different companies utilizing their respective designs. As such, a need has developed so as to allow for the adaptation of the water containers to the various endoscope systems which are offered. Any standardization that can be achieved will eliminate the need to maintain an inventory of products for each of the various types of water bottles available.

Figure 5A:
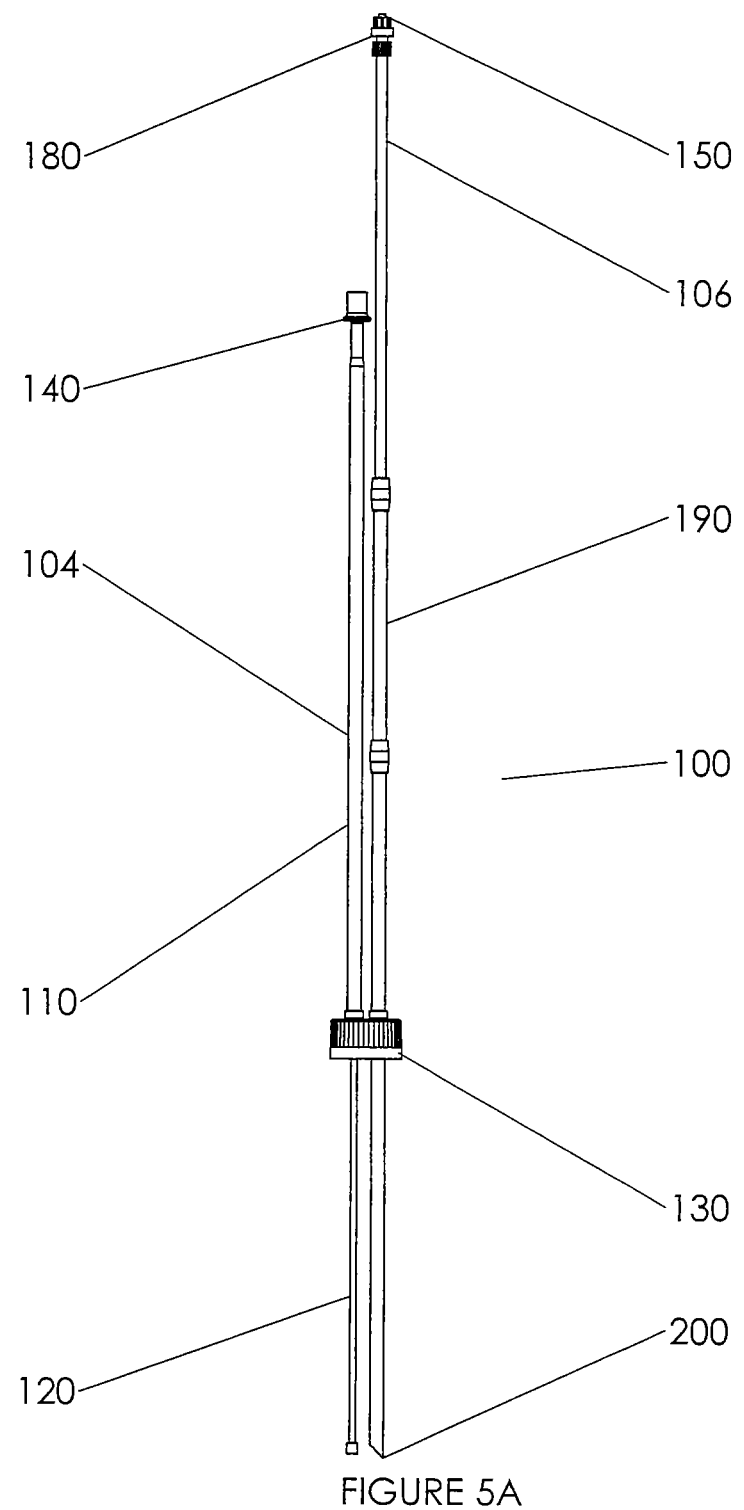
FIG. 5A is an illustrative embodiment of a combined irrigation and air/water tube set.

FIG. 5A shows an illustrative embodiment of a combined tube set 100. Combined tube set 100 includes air/water tube set 104, irrigation tube set 106, bottle cap 130, air/water connector 140, and irrigation connector 150. Irrigation connector 150 can be a universally adaptable connector, such as a luer connector. Irrigation connector 150 can alternately be a connector designed for direct connection to the endoscope. The air/water tube set 104 is shown as a water tube 120 extending through air tube 110 from bottle cap 130 to air/water connector 140. While air/water connector 140 is shown as a connector suitable for connection to an Olympus endoscope, it should be recognized that any suitable connector may be utilized to facilitate use of the various types and/or brands of endoscopes.

Air/water connector 140 and/or irrigation connector 150 can alternately be a universally adaptable connector design. Further, in other embodiments, the tubing arrangement of the tube sets may also be modified to accommodate various types and/or brands of endoscopes. For example, the air/water connector 140 and the irrigation connector 150 may utilize any variety of connector that is suitable for connecting combined tube set 100 to any type or brand of endoscope or a fitting may be mated with an adapter body that allows a tube set to be utilized with a particular brand and type of endoscope (e.g. U.S. Pat. Nos. 6,210,322 and 6,485,412). In some embodiments, a universal connector or adapter connected to the endoscope may receive both air/water connector 140 and the irrigation connector 150. For example, combined tube set 100 may be suitable for connection with a Fujinon AJ-510 or Byrne Medical 100141 adapter. While water tube 120 extends through air tube 110 in the embodiment shown, in some embodiments the air tube and water tube may be separated i.e. the water tube is not contained within the air tube. In a separated air and water tube arrangement, air/water connector 140 may provide a fitting that may be mated with an adapter body that provides a connector that is suitable for connection with an endoscope utilizing a concentric air and water tube arrangement. Further, in some embodiments, the universal connector may be moved away from the endoscope as shown in FIG. 5C. The embodiment in FIG. 5C shows an embodiment in which the irrigation tube set 106 and the air and water tube set 104 connect to an adapter 250. The adapter is specifically designed to connect to a particular model of endoscope. The adapter includes an air/water connector 140 and an auxiliary water connector 150. The adapter input connector 240 receives the irrigation tube set 106 and the air and water tube set 104. This connector is identical for all models of the adapter so that the same irrigation tube set and air and water tube set designs can be used regardless of endoscope model. The irrigation tube 255, water tube 260, and air tube 265 pass water and air between the tube sets and the endoscope 72 light guide connector.

In the air/water tube set 104, water tube 120 extends from air/water connector 140 through the bottle cap 130. Air tube 110 has a larger diameter than water tube 120 and extends from air/water connector 140 to bottle cap 130. Air tube 110 and water tube 120 may be made from a plastic material, elastomeric material, or any suitable material or combination of materials. Air tube 110 and water tube 120 may be secured to air/water connector 140 by ultraviolet gluing, any suitable adhesive, or any suitable attachment means. While water tube 120 passes through bottle cap 130, air tube 110 may be secured to bottle cap 130 by ultraviolet gluing, any suitable adhesive, or any suitable attachment means. Because air tube 110 has a larger diameter than water tube 120, an annular air passage is created between the outer surface of water tube 120 and the inner surface of air tube 110. The annular air passage extends from bottle cap 130 to air/water connector 140.

Bottle cap 130 can be secured to the neck of a water bottle (not shown), thereby allowing an end of water tube 120 to extend into the water bottle. Bottle cap 130 can be made of a plastic material, elastomeric material, and/or any suitable material or combination of materials. Water tube 120 may have an anchor 160 attached to one end to weigh down water tube 120 into the liquid contained in the water bottle. Weight 160 serves to assure that end 170 of water tube 120 will reside adjacent to the bottom of the sterile water bottle. Weight 160 provides an opening (not shown) that allows fluid to pass through water tube 120 to air/water connector 140. In some embodiments, weight 160 may be omitted. Weight 160 can be ultraviolet glued to end 170 of water tube 120 or secured by any suitable adhesive or any suitable attachment means.

Bottle cap 130 has inner threads which are particularly adapted for joining with the threads of a variety of different water bottles, as discussed in more detail below. Bottle cap 130 may include one or more gaskets (not shown) to facilitate a substantially air tight seal between bottle cap 130 and a water bottle. When bottle cap 130 is secured to a water bottle and air/water connector 140 is connected to an endoscope, air may pass from the endoscope to the water bottle via the annular air passage created between the outer surface of water tube 120 and the inner surface of air tube 110. Note that in other embodiments the tubes may be separate. Because bottle cap 130 creates an air tight or nearly air tight seal, forcing air into the water bottle creates pressure in the bottle that forces water through a first end of water tube 120 having weight 160 towards a second end of water tube 120 having air/water connector 140.

Irrigation tube set 106 is also connected to bottle cap 130 to provide combined tube set 100. Irrigation tube set 106 include irrigation connector 150, back flow valve(s) 180, and flexible tubing section 190. A first end of irrigation tube set 106 provides irrigation connector 150, which may be connected to an endoscope. In contrast to air/water tube set 104, irrigation tube set 106 provides a single tube. Irrigation tube set 106 may be made from a plastic material, elastomeric material, or any suitable material or combination of materials.

Irrigation tube set 106 may include one or more backflow valves 180 to prevent backflow of water into the water bottle. Irrigation tube set 106 may include flexible tubing section 190, which is insertable into a peristaltic pump. In the embodiment shown, backflow valves 180 are place on opposite ends of flexible tubing section 190. However, in other embodiments, one or more backflow valves 180 may be placed on the end of the irrigation tube set 106 closer to bottle cap 130 or the endoscope. Backflow valves 180 prevent or limit backflow of water back into the water bottle, thereby reducing the risk of potential contamination of the sterile water in some embodiments, backflow valves may also be utilized in the air/water tube set 104.

Tubes of the irrigation tube set 106 may be secured to bottle cap 130, irrigation connector 150, and/or backflow valve(s) 180 by ultraviolet gluing, any suitable adhesive, or any suitable attachment means. When bottle cap 130 is placed on a water bottle, water source end 200 of irrigation tube set 106 extends into the water bottle. As with water tube 120 of air/water tube set 104, water source end 200 of irrigation tube set 106 may include an anchor (not shown) to weigh down water source end 200 towards the bottom of the sterile water bottle.

Separated tube sets shown in FIGS. 1 and 3 require two separate water bottles that may not be fully utilized during the use of an endoscope. When the use of the endoscope is complete, the two water bottles may be discarded to prevent future contamination of the water and/or equipment. Further, if the tube sets are disposable, two tube sets are discarded. If the tube sets are reusable, the equipment must be manually or automatically cleaned and disinfected or autoclaved to sterilize the equipment for future use. In contrast, combined tube set 100 allows a water source for irrigation and rinsing to be provided by a single water bottle, thereby minimizes waste. Further, combined tube set may be made of a low cost, disposable material so that labor and cost associated with cleaning and autoclaving is avoided.

Figure 5B:
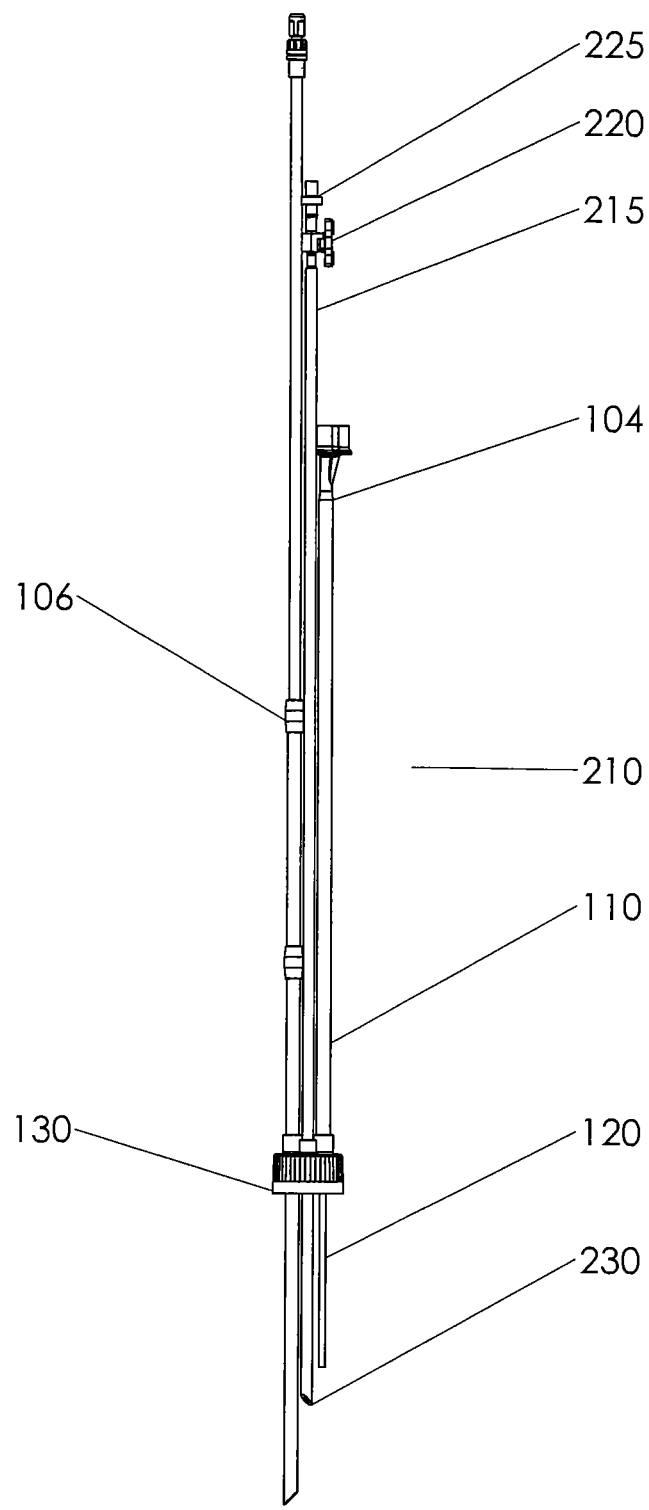
FIG. 5B is an illustrative embodiment of a combined irrigation, air/water, and gas tube set.
Figure 5C:
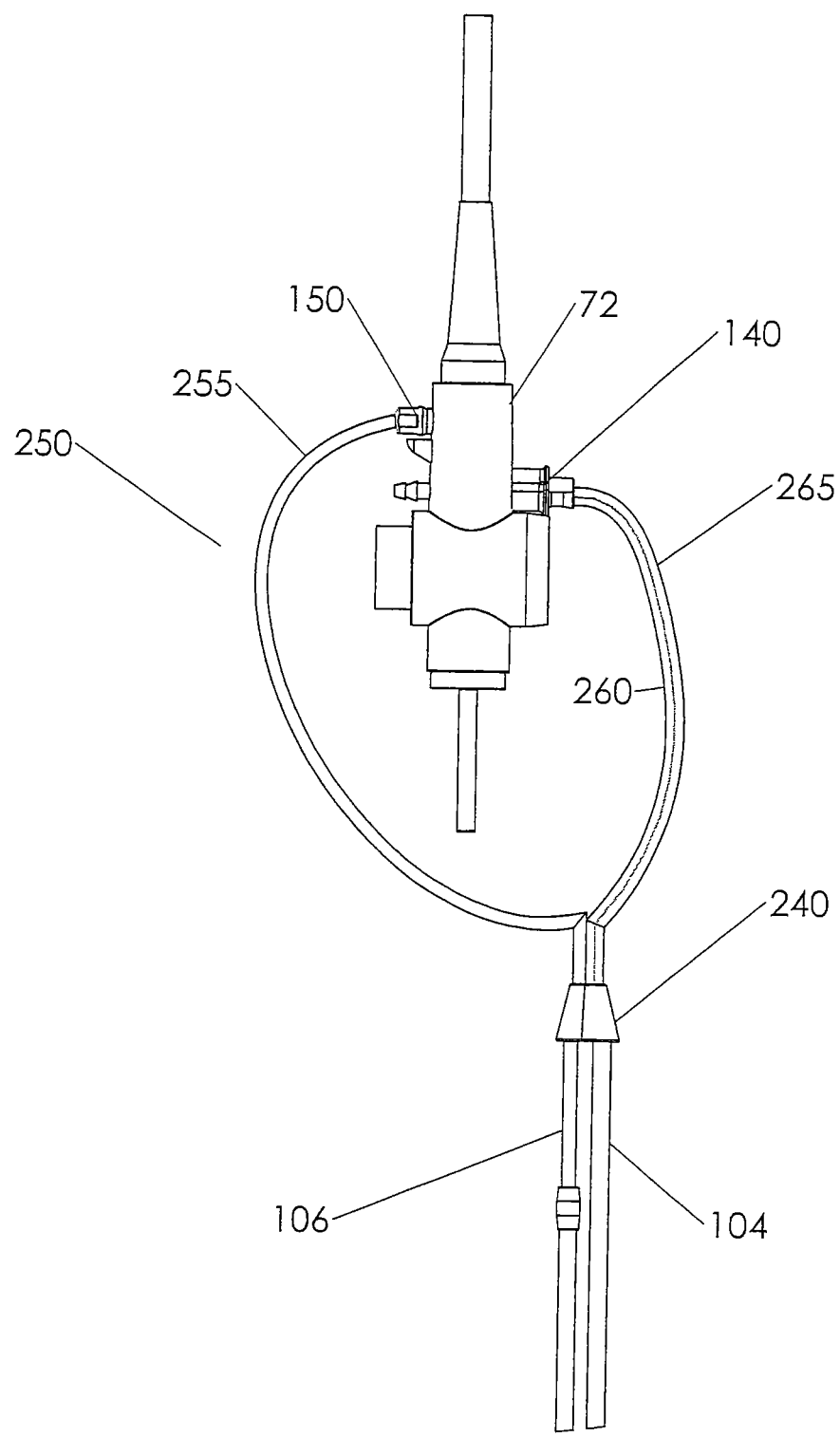
FIG. 5C is an illustrative embodiment of a universal connector for a combined irrigation and air/water tube set.

FIG. 5B is an illustrative embodiment of a combined irrigation, air/water, and gas tube set 210. Combined irrigation, air/water, and gas tube set 210 may provide an air/water tube set 104, irrigation tube set 106, and bottle cap 130 similar to the tube set shown in FIG. 5A. Additionally, combined irrigation, air/water, and gas tube set 210 also provides gas tube set 215. Gas (e.g. air, carbon dioxide, or the like) may be supplied to the bottle by gas tube set 215 attached to bottle cap 130. Gas supply connector 225 may be connected to a gas source and gas valve 220 may be utilized to open and close the flow of gas into a water bottle. Gas valve 220 is optional and may not be utilized in other embodiments. When gas valve 220 is open, gas flows into the bottle through the gas tube set 215, pressurizes the bottle, and passes from the bottle cap 130 to the endoscope via the annular passage created between the outer surface of water tube 120 and the inner surface of air tube 110. While end 230 of gas tube set 215 extends through bottle cap 130 in the embodiment shown, in other embodiments end 230 may stop at bottle cap 230.

Figure 6A:
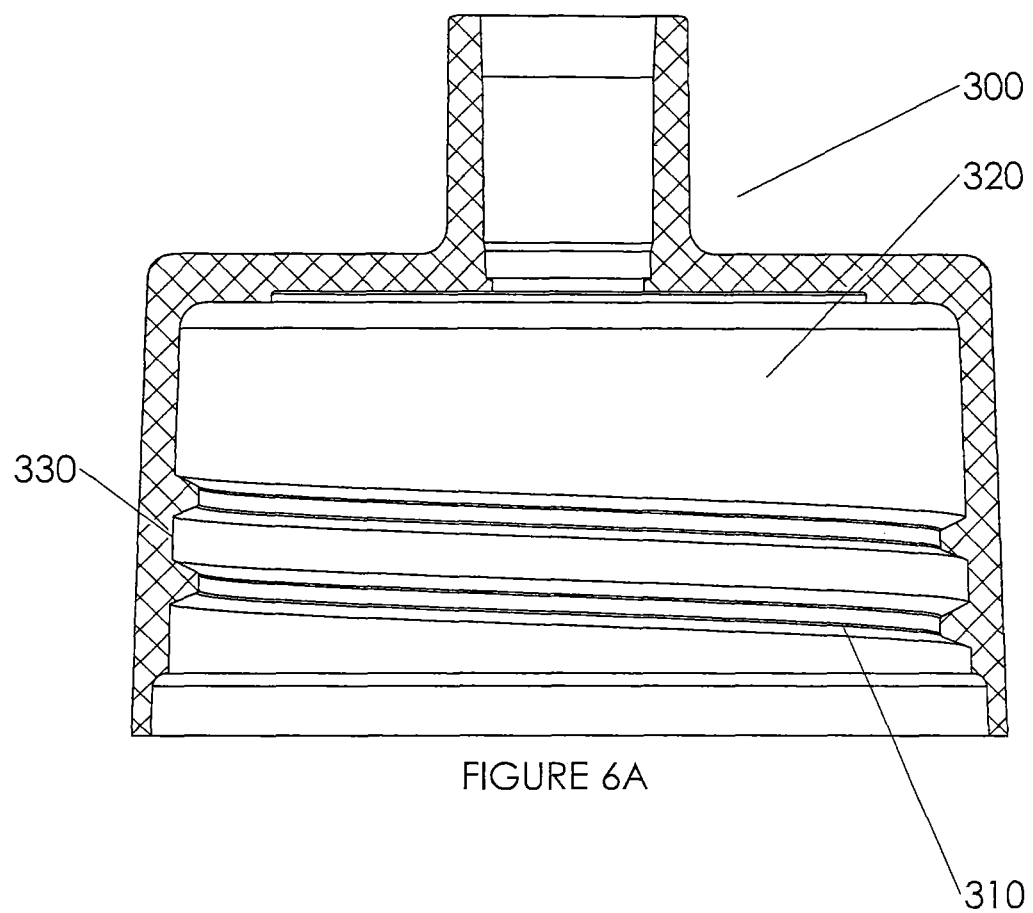
FIG. 6A is an illustrative embodiment of a universal fit bottle cap.
Figure 6B:
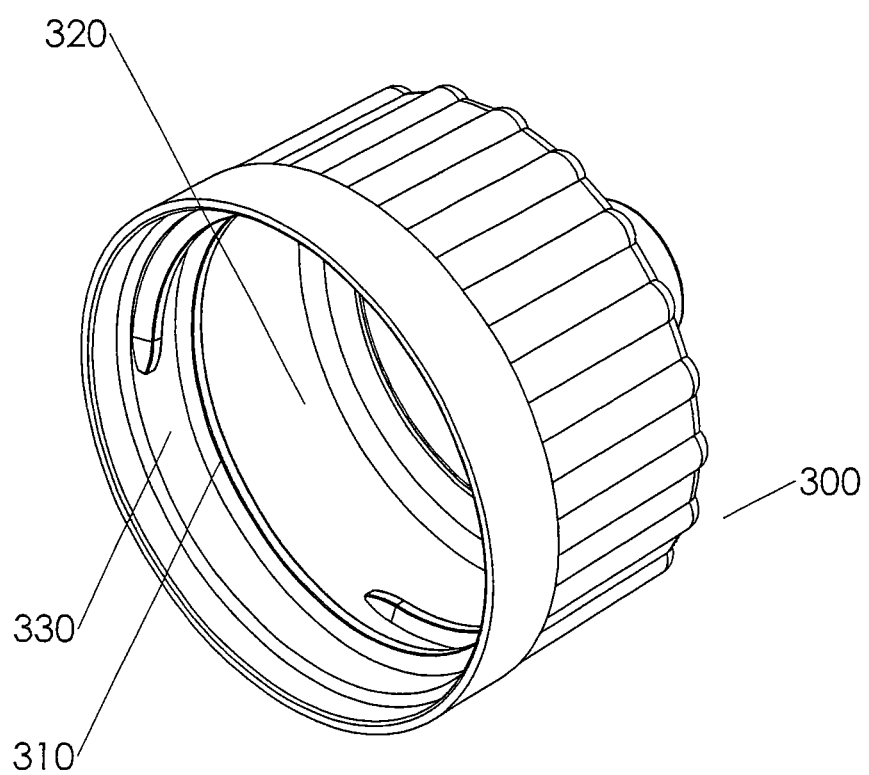
FIG. 6B is an isometric view of an illustrative embodiment of a universal fit bottle cap.

FIG. 6A is an illustrative embodiment of a universal fit bottle cap 300, and FIG. 6B is an isometric view of an illustrative embodiment of a universal fit bottle cap 300. Bottle cap 300 may optionally utilize a liner or seal (not shown) to create an air tight seal with a water bottle. Thread(s) 310 on the inner surface of universal fit bottle cap 300 have specific cross-sectional geometry and thread pitch that allows it to be utilized with a variety of water bottles. The material from which the cap is made has structural and tribological properties (including Young's modulus and coefficient of friction). The dimensions, geometry and pitch of the threads, and material properties of universal fit bottle cap 300 allow it to mate to any of several commercially available water bottles even though the designs of these water bottles vary.

Similarly, the liner material has structural and tribological properties (including durometer and coefficient of friction). The liner also has a certain cross-sectional profile. The combined effect of the liner's profile and material properties allow it to form a seal between the bottle cap and any of several different water bottles. Specifically, the inner surface of the liner is shaped so as to continuously contact the bottle around its full circumference, thus sealing the system. Given that different bottles have rims or ridges of different diameters and at different heights relative to their threads, the liner has a varying inner diameter designed to accommodate each bottle design by contacting it at the appropriate height and diameter. The liner may, if desirable, use gaps along the surface contacting the cap in order to allow the liner to conform to the bottle rim. The liner may be formed separately and inserted into the bottle cap. Alternately, the liner may be formed directly into the bottle cap, such as by the process of over molding. Alternately, the bottle cap and the liner may be formed as one contiguous body. Additionally, the liner may also be used to form an air-tight seal between the bottle cap and the aforementioned tube sets.

The bottle cap is preferably made from a rigid polymer such as acrylonitrile butadiene styrene (ABS), polyvinyl chloride (PVC), polystyrene, or polycarbonate. In the embodiment shown, thread 310 has a pitch of 0.160", and thread 310 may travel through a certain number of revolutions. Creating too many revolutions will limit the bottle geometry with which the bottle cap can mate. However, creating too few revolutions can prevent the cap from making a reliable connection to the water bottle. In the embodiment shown, thread 310 travels 1.75 revolutions. The inner diameter of universal fit bottle cap 300 above and below the threads 310 should preferably be wide enough to allow the top of the bottle to pass into region 320 above threads 310. If the inner diameter of universal fit bottle cap 300 is to narrow, it will not be able to travel as far onto the bottle as needed in order to engage the liner for an air-tight seal.

Thread 310 should have a cross section which is thicker at the base (where it meets the wall of the bottle cap) and thinner at the inner surface (nearest the bottle neck). This geometry would resemble a trapezoid. In the present embodiment, the innermost surface should have a thickness of about 0.035" and the thickest portion (near the wall) should have a thickness of about 0.090".

The thread has a minor diameter, measured as the distance across the thread at its surface that extends farthest from the wall of the bottle cap. The thread has a major diameter, measured as the distance across the thread at its base where it joins the wall of the bottle cap. In one embodiment of universal fit bottle cap 300, threads 310 have a minor diameter of about 1.375" and a major diameter of about 1.490". In another embodiment of universal fit bottle cap 300, threads 310 have a minor diameter of 1.300" and a major diameter of about 1.420". Surface 330 on which the threads are formed (the inner cylindrical surface of the bottle cap) is tapered at an angle of about 2 degrees so that its diameter is slightly larger at the opening of the cap than at the opposite end of that surface. In order to ensure smooth movement of universal fit bottle cap 300 as it is threaded onto the bottle, threads 310 may not have blunt edges and corners in some embodiments. The corners of the trapezoidal geometry at either end of the 0.035" wide inner surface may be rounded with a fillet whose radius is about 0.005". The two ends of threads 310 may taper in a ramp-like fashion to provide a smooth transition from the thread's minor diameter to it's minor diameter.

Figure 6C:
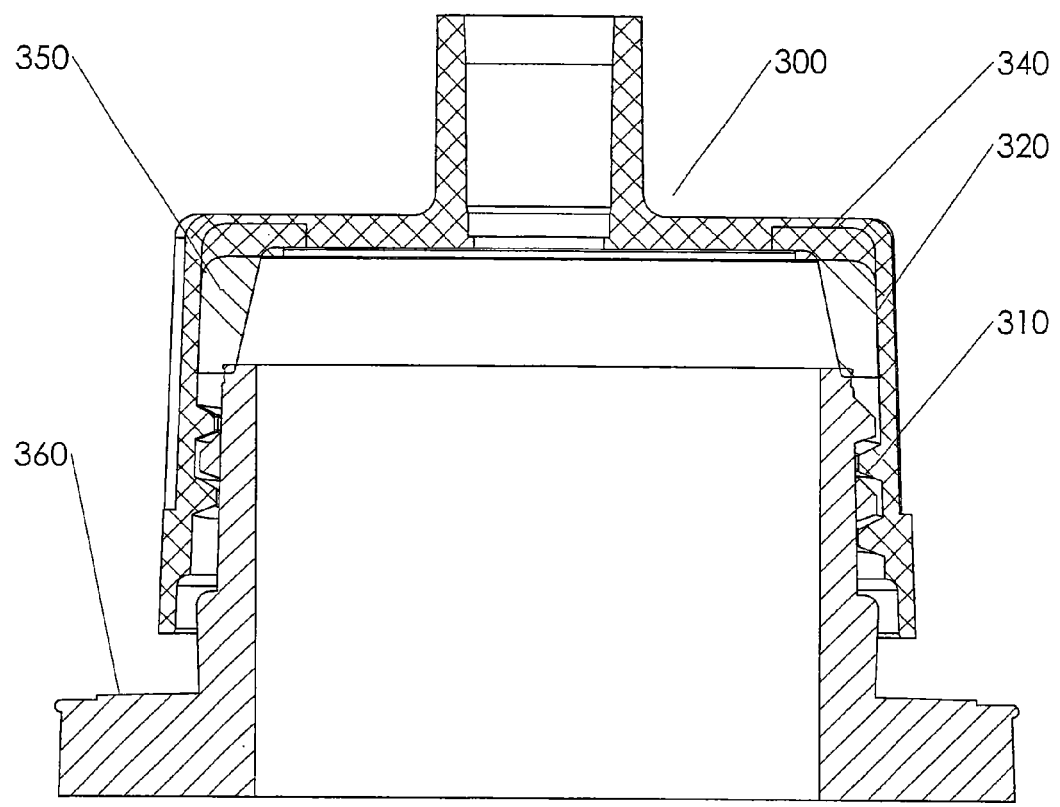
FIG. 6C is an illustrative embodiment of universal fit bottle cap threaded on a bottle.

FIG. 6C is an illustrative embodiment of universal fit bottle cap 300 threaded on a bottle. Liner 350 resides in region 320 between threads 310 and top end 340 of universal fit bottle cap 300. Liner 350 engages bottle 360 when universal fit bottle cap 300 is threaded a sufficient distance on to the neck of a bottle. Bottles from different manufacturers vary significantly in (1) distance from the bottle thread to the top rim, (2) distance from the bottle thread to the bottle neck's largest outer diameter; (3) the diameter of the bottle's rim; and (4) the bottle neck's largest diameter. The liner is designed to mate to one or both of the largest neck diameter and the top rim for the various bottle geometries. Thus, the liner has an inner surface with an inner diameter that varies over its length. The liner's varying inner diameters and their positions relative to the bottle cap threads cause the liner to engage the bottle neck or rim sufficiently to form an airtight seal.

In order to maintain pressure within the system to deliver gas for insufflation and water for rinsing the lens, the system must be reasonably air tight. The seal between the bottle and the bottle cap may be maintained by a liner which is a flexible member of the bottle cap assembly. This liner maintains contact with the cap and the bottle by deforming as it is squeezed between the rigid materials of the cap and the bottle. Of particular importance is the geometry of the liner surfaces that are intended to maintain contact with the bottle and cap. A single liner design will be able to maintain an air-tight seal between multiple cap designs and multiple bottle designs. However, in some embodiments, multiple liners may be utilized. In other embodiments, the cap and liner may be integrated into a one piece member such that the cap is a flexible member which forms a seal with the bottle, including bottles of differing geometry.

The bottle cap and the bottle neck have mating threads. As the cap is threaded onto the bottle neck, the liner engages the bottle neck or the bottle throat and forms the seal. Since bottle thread geometries vary, a cap and liner design may engage sufficiently with a variety of bottle geometries sufficiently to hold the cap in place, thus compressing the liner to form a seal with the bottle.

Figure 6D:
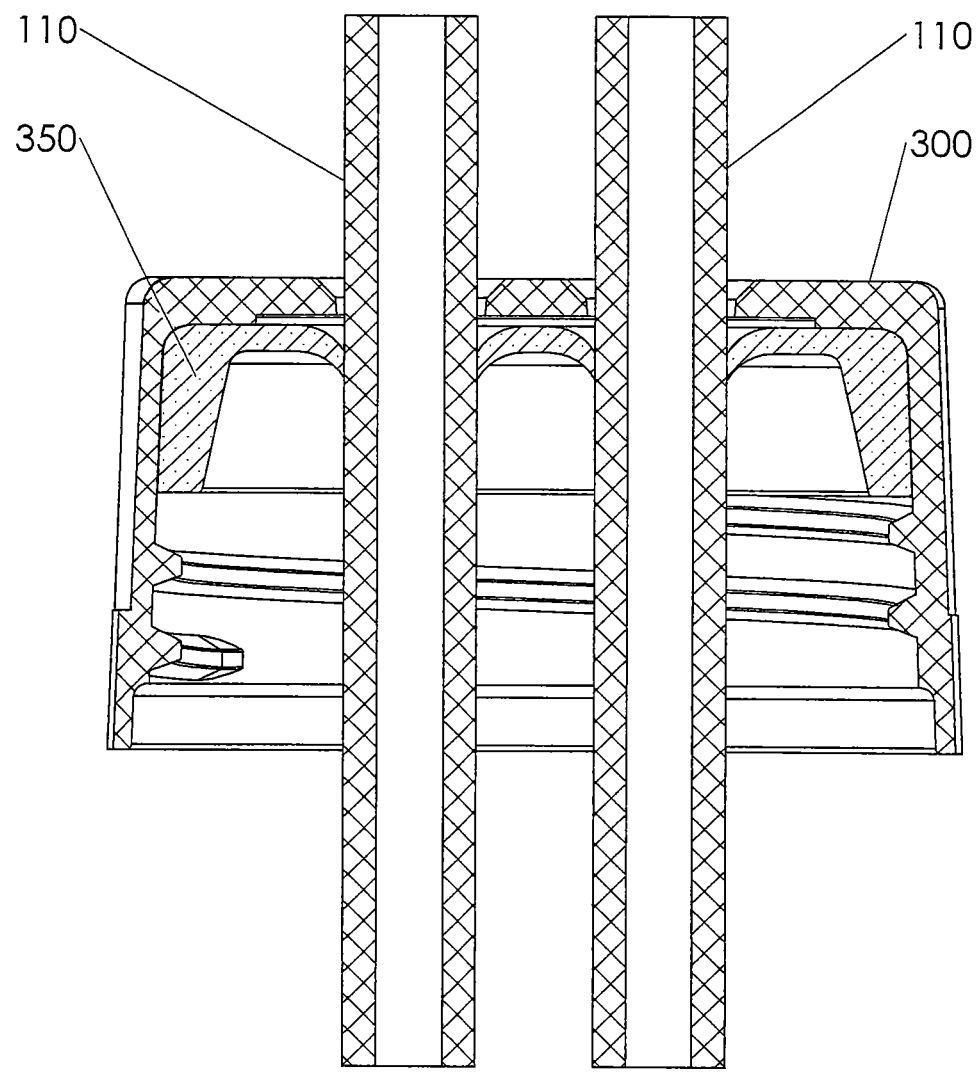
FIG. 6D is an illustrative embodiment of a bottle cap and liner.

FIG. 6D is an illustrative embodiment of a bottle cap 300 and liner 350. Another point at which the system must be sealed is between the cap 300 and the tubes 110 connected to the bottle. This also includes the bond between the cap and any other tubes that pass through it necessitating a seal to maintain system pressure. In some cases, the tube may be bonded to the cap with an adhesive bond, a solvent bond, or a mechanical lock such as a swaged fitting. However, in other embodiments, the structural connection between the tube and the cap can make use of a flexible liner so that no adhesive or solvent bond between the tube and cap is needed. This liner may occupy the space between the cap and the tube so that the liner is compressed and thus forms an air-tight seal. Alternatively, the liner may surround the tube in the region above or below the bottle cap, forming a seal by constricting the tube. Given the proper geometry, the liner's seal against the tube's outer surface may increase its constriction as the pressure within the system increases, forcing the flexible liner material against the outer wall of the tube.

Figure 7:
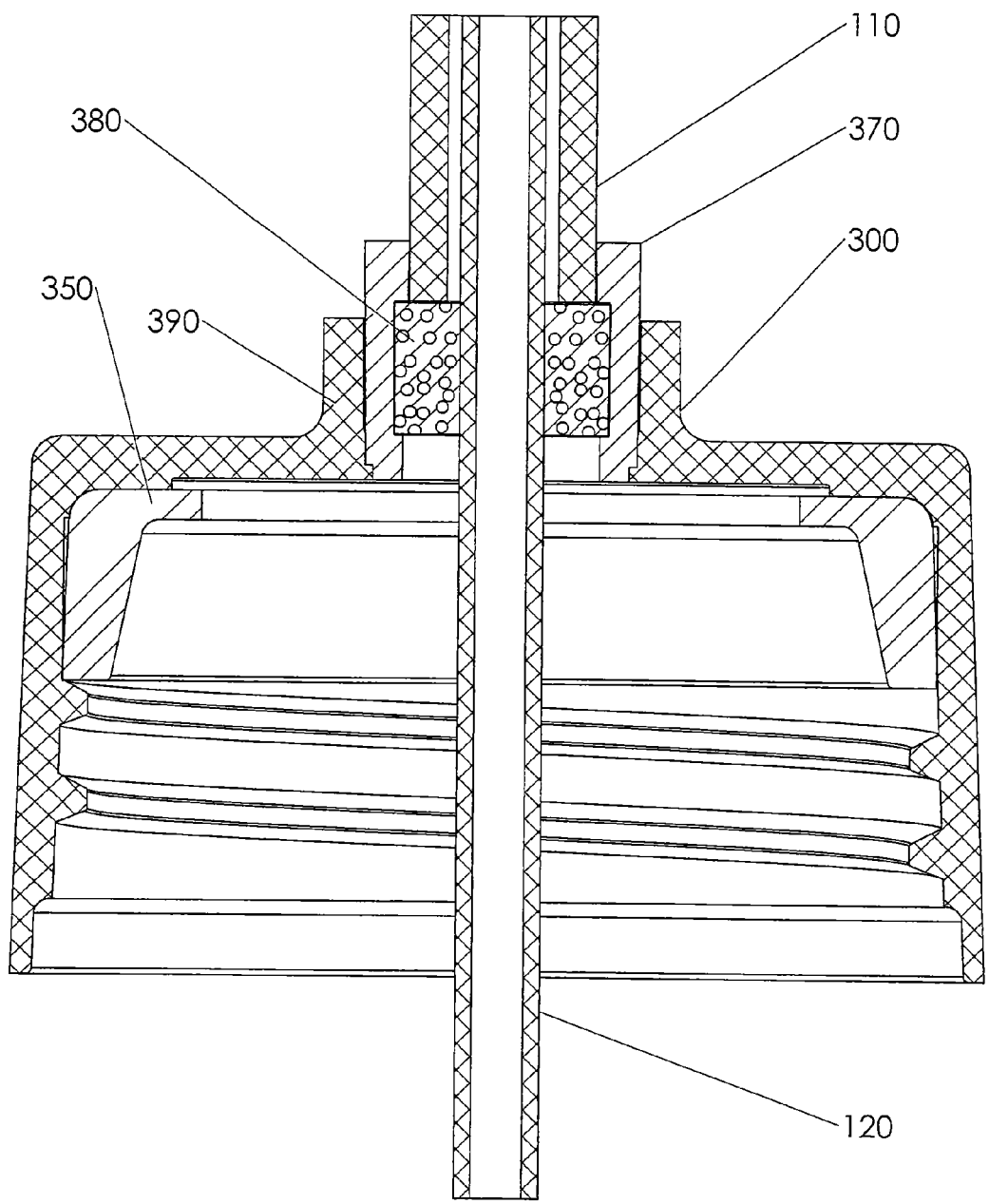
FIG. 7 is an illustrative embodiment of air filter incorporated into a bottle cap.

FIG. 7 is an illustrative embodiment of air filter incorporated into a bottle cap. Air tube 110 stops in filter housing 370. Filter housing 370 fits into a nipple 390 of the bottle cap 300. Water tube 120 passes through the filter medium 380. Water tube 120 and filter medium 380 may be in contact to properly seal the air passageway.

Figure 8:
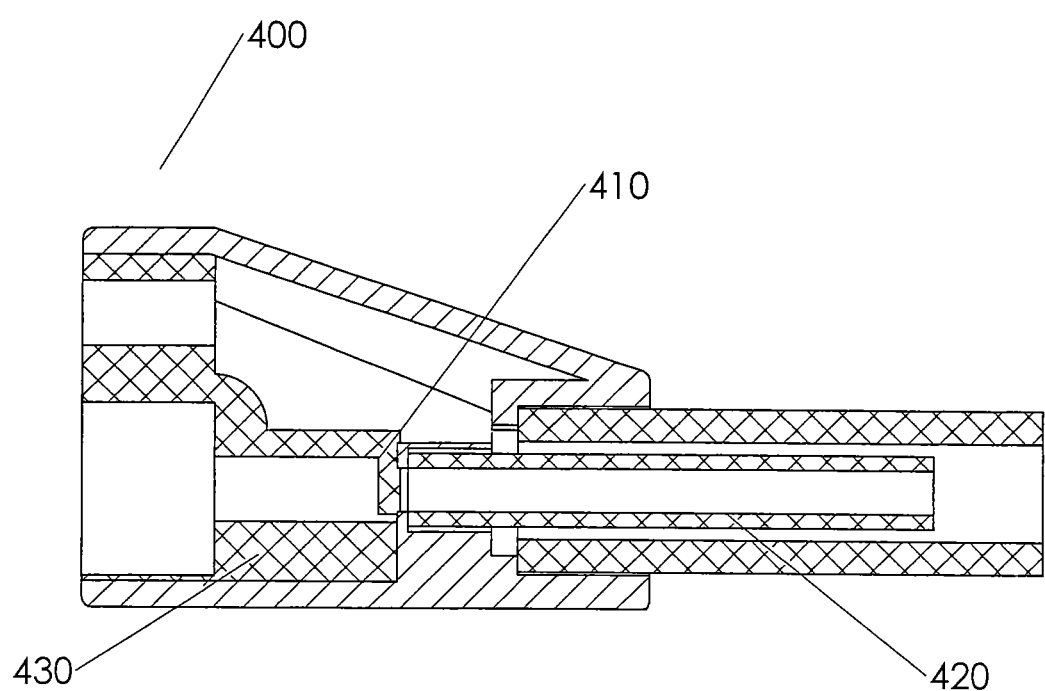
FIG. 8 is an illustrative embodiment of an air/water connector with a check valve.

As water is removed from a water bottle, air must be allowed to flow into the bottle. In some embodiments, air may enter the bottle through a filter (microbial, HEPA, etc.) so as to maintain the sterility of the air and water in the bottle. the irrigation system preferably includes a backflow valve or check valve to ensure that contaminated fluid from the patient does not enter the irrigation system i.e. unidirectional flow from the bottle to the endoscope and not in the reverse direction. The irrigation tube that feeds water to the endoscope is typically used on multiple patients in the course of a day, so contamination from a patient that enters the tubing may be passed to subsequent patients. Thus, a check valve is desirable for maintaining the sterility of the water in the bottle and in the tube set. FIG. 8 is an illustrative embodiment of an air and water connector 400 with a check valve. The connector employs a movable flap 410 in the water flow path to prevent water from flowing from the endoscope into the water tube 420. The flap 410 may be formed from a soft, flexible material such as a thermoplastic elastomer. The flap may be formed from the same body that forms a seal around the water intake tube of the endoscope air/water receptacle. When the pressure in the water tube 420 of the tube set is higher than that in the endoscope's water intake tube (i.e., when the bottle is pressurized and the endoscope's lens rinsing water valve is opened), water will flow from the tube set into the endoscope, forcing the moveable flap 410 open. When there is no pressure differential pressure, the flap 410 comes to rest, preferably in a position that closes or nearly closes the flow path. When the pressure in the water tube 420 of the tube set is lower than that in the endoscope's water intake tube (i.e., when the endoscope's lens rinsing water valve is opened and the pressure in the patient's anatomical lumen is higher than the pressure in the bottle), water movement will force the moveable flap 410 closed. When the moveable flap 410 closes, it may close against a feature of the sealing body. The moveable flap 410 may also close against the end of the water tube 420 or a structural member of the connector assembly 400. The connector also includes a body 430 that seals around the water inlet tube of the endoscope so that water does not leak to the outside or to the air flow path. It should be noted that some endoscope designs accept water through some other means than a protruding tube (such as a hole to which the connector must mate by means of a gasket); the valve described here would similarly prevent retrograde flow in a design compatible with such an endoscope. In some embodiments, the valve mechanism described here may also be used to prevent retrograde flow of air (or other gasses) through the tube set and endoscope. In embodiments that accept air flow from the endoscope to pressurize the bottle, the valve would only allow air flow from the endoscope to the bottle and would prevent air flow from the bottle to the endoscope. In embodiments that accept air from a separate air source, air would flow from the bottle to the endoscope and the valve would prevent flow in the opposite direction.

Figure 9A:
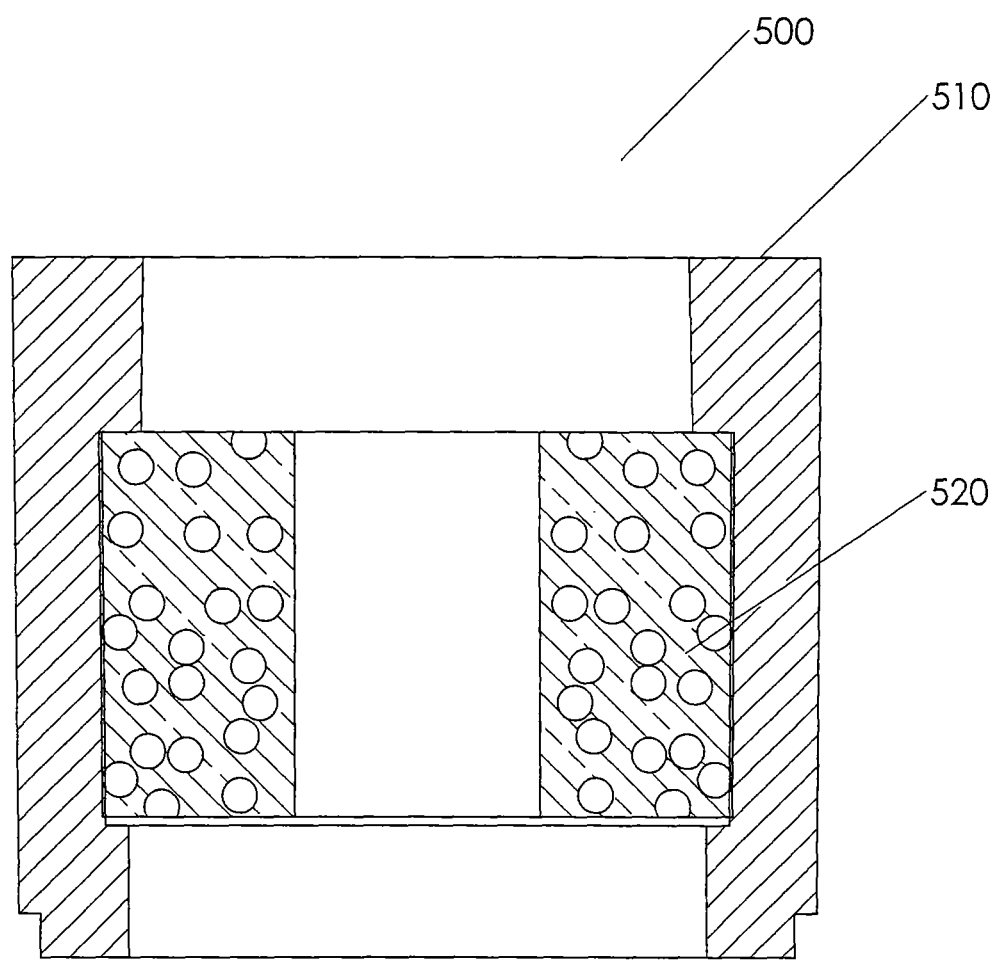
FIG. 9A is an illustrative embodiment of an inline air filter assembly.
Figure 9B:
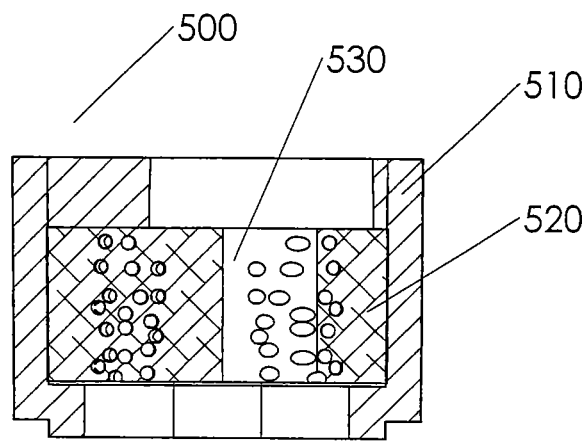
FIG. 9B is an illustrative embodiment of an inline air filter assembly with an offset water tube passage.
Figure 9C:
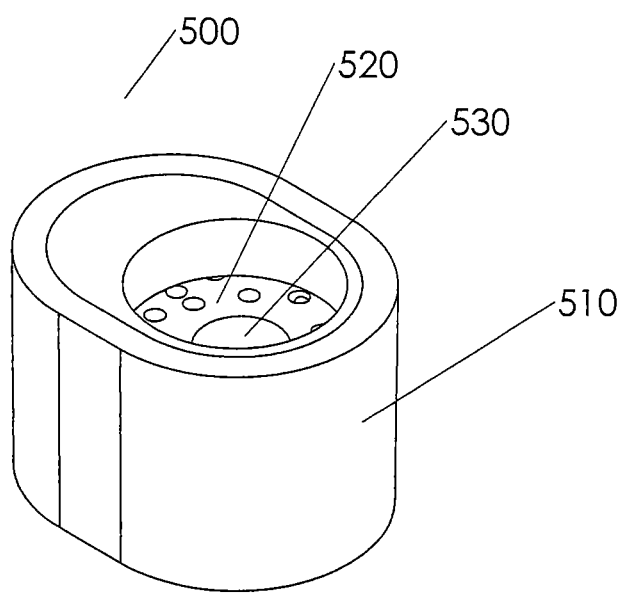
FIG. 9C is an illustrative embodiment of an inline air filter assembly with an offset water tube passage.

FIG. 9A is an illustrative embodiment of an inline air filter assembly 500. From a biological safety perspective, the air that enters the water bottle may be filtered. Air that enters the water bottle without being filtered may carry infectious microorganisms. The illustrated embodiment is a filter that forms a part of the connector that joins the air and water tubes to the bottle cap. As illustrated, the filter is formed as an annular member that surrounds the water tube and fills the space between the air tube and the water tube. The filter is composed of some porous medium 520. Depending on the structural properties of the filter medium, the filter assembly may include a structural member 510 with surfaces for bonding to the bottle cap and the water tube. The water tube may pass through the center of the filter, as illustrated, or it may pass to the side of the filter. All air passing through the tube is filtered. As illustrated, the filter assembly is located where the air tube joins the bottle cap. In other embodiments, the filter assembly may also be located at the end of the air tube that connects to the air/water connector. In such an embodiment, the filter may be incorporated as a structural member of the air/water connector. FIG. 9B is a cross-sectional illustrative embodiment of an inline air filter assembly 500 with an offset water tube passage 530 in porous medium 520 which is encased in structural member 510. FIG. 9C is an illustrative embodiment of an inline air filter assembly 500 with an offset water tube passage 530 in porous medium 520 which is encased in structural member 510.

Figure 10:
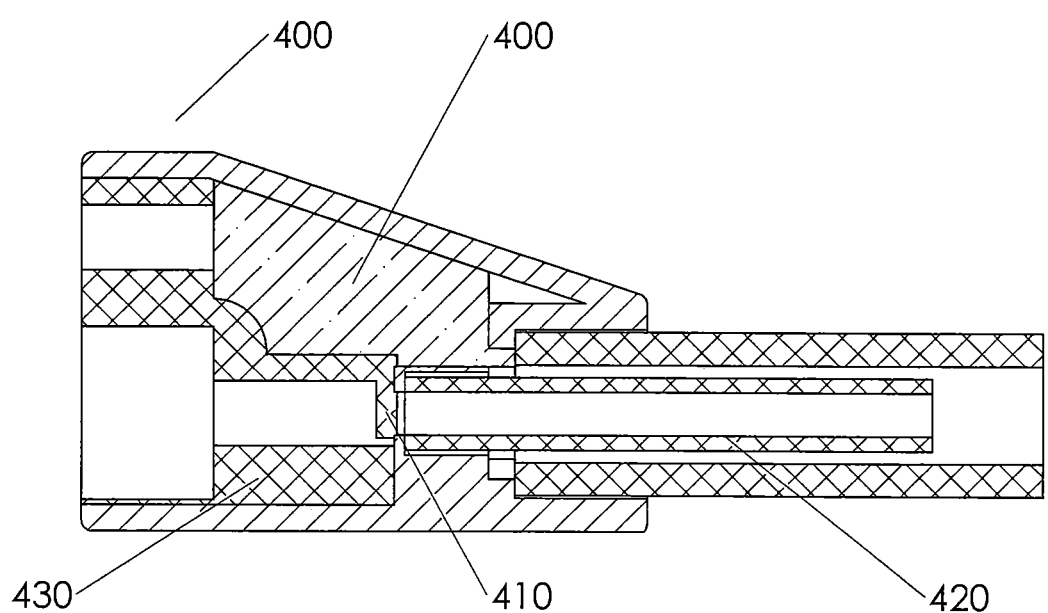
FIG. 10 is an illustrative embodiment of an air and water connector with a check valve and an inline air filter.

FIG. 10 is an illustrative embodiment of an air and water connector 400 with a check valve 410 and an inline air filter 440.

Figure 11A:
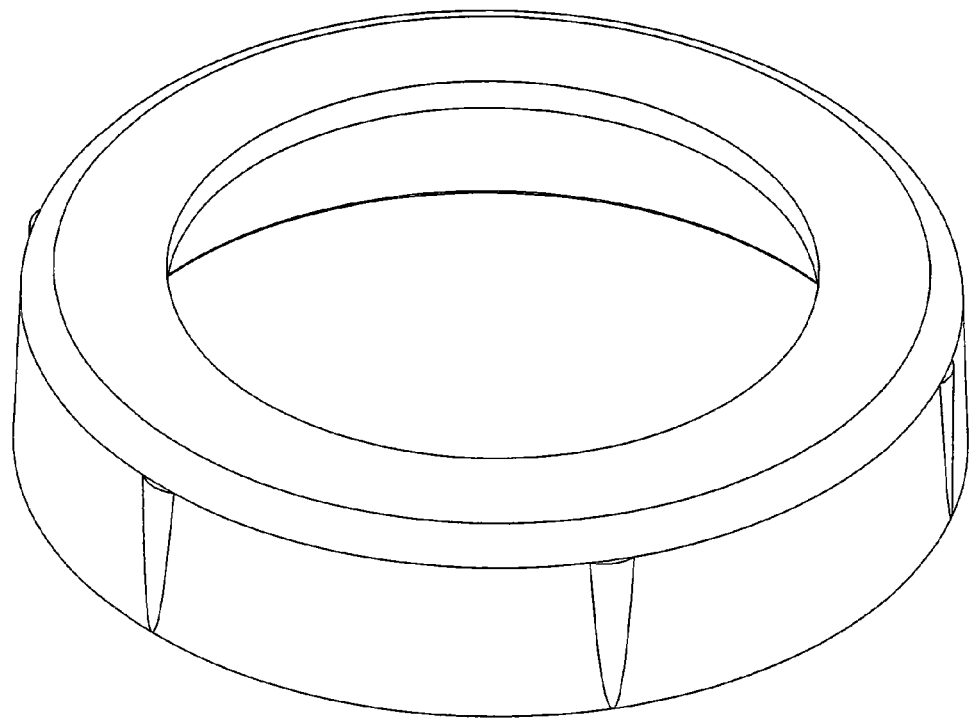
FIG. 11A is an illustrative embodiment of a liner with a substantially L-shaped cross section.
Figure 11B:
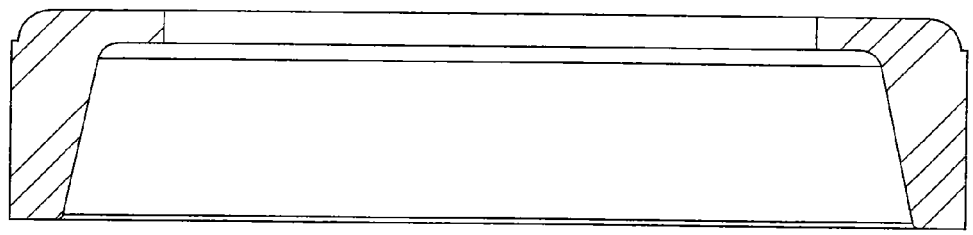
FIG. 11B is an cross sectional view of an illustrative embodiment of a liner with a substantially L-shaped cross section.

FIG. 11A is an illustrative embodiment of a liner with a substantially L-shaped cross section. FIG. 11B is an cross sectional view of an illustrative embodiment of a liner with a substantially L-shaped cross section.

The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

The invention claimed is:

1. A cap comprising: a thread on an inner surface of said cap; and a one-piece liner formed from a single material inside said cap capable of sealing on multiple surfaces, said liner comprising a top surface that engages an upper wall of the cap and an outer surface being substantially vertically oriented that engages a side wall of said cap and said liner comprising an inclined inner surface to provide a tapered configuration, a gap being formed between the upper wall of the cap and the top surface of the liner opposing the upper wall, said side wall extending transversely from said upper wall, wherein said upper wall comprises at least two openings and said top surface comprises at least one aperture receiving a tube set assembly having a first tube set comprising an air/water tube, a second tube set comprising an irrigation tube, and a third tube set comprising a gas tube, one of the at least two openings and the at least one aperture receives the first tube set, one of the at least two openings and the at least one aperture receives the second tube set or the third tube set, the air/water tube comprising a water tube and an air tube in a coaxial arrangement, the water tube having a diameter smaller than the air tube, the irrigation tube and the gas tube, the cap having a reinforced rim above each opening to receive the first tube set, the second tube set and the third tube set, wherein the inclined inner surface of the liner is configured to engage a variety of bottle necks of varying heights and diameters, and the liner has an inner diameter having a tapered configuration, which is not constant, the liner comprising at least one aperture to receive the first, the second and the third tube set.

2. The cap of claim 1, wherein the cap is for water bottles for medical applications.

3. The cap of claim 2, wherein the cap is for water bottles for endoscopic systems.

4. The cap of claim 1, wherein the cap and the liner are made of the same material.

5. The cap of claim 1, wherein the cap and the liner are made of different material.

6. The cap of claim 1, wherein said liner contains at least one rib on the external surface.

7. The cap of claim 1, wherein the cap is made from a plastic material, elastomeric material, thermoplastic material, rigid polymer, or combination thereof.

8. The cap of claim 1, wherein the cap is made of methyl methacrylate acrylonitrile butadiene styrene (MABS), acrylonitrile butadiene styrene (ABS), polyvinyl chloride (PVC), polystyrene, polycarbonate, polypropylene, rubber, nylon, or silicon.

9. The cap of claim 1, wherein the cap and the liner are one contiguous body.

10. The cap of claim 1, wherein said inner diameter, which is not constant, decreases axially toward said top end.

11. The cap of claim 1, wherein the thread is a positive thread.

12. The cap of claim 1, wherein the liner comprises a substantially L-shaped cross section.

13. The cap of claim 1 further comprising an air filter.

14. The cap of claim 1, wherein the thread has a trapezoid geometry comprising a first base and a second base, wherein the first base is larger than the second base and wherein the first base is adjacent to the wall of the cap.

15. The cap of claim 1, wherein the thread comprises a first diameter and a second diameter, wherein the first diameter is larger than the second diameter.

16. The cap of claim 1, wherein the thread comprises about 1.75 revolutions.

17. The cap of claim 14, wherein the trapezoidal geometry comprises rounded corners.

18. A cap comprising a thread on an inner surface, a one-piece liner formed from a single material positioned above the thread, said liner comprising a top surface that engages an upper wall of the cap and an outer surface being substantially vertically oriented that engages a side wall of said cap, a gap being formed between the upper wall of the cap and a top surface of the liner opposing the upper wall, said side wall extending transversely from said upper wall, said liner comprising an inclined inner surface to provide a tapered configuration such that the inclined inner surface of the liner is configured to engage a variety of bottle necks of varying heights and diameters; wherein said upper wall comprises at least three holes and said top surface comprises at least one aperture, one of the at least three holes and the at least one aperture receives an air/water tube, one of the at least three holes receives an irrigation tube, and the air/water tube comprises a water tube and an air tube in a coaxial arrangement, the water tube having a diameter smaller than the air tube and the irrigation tube, wherein the liner has an inner diameter having a tapered configuration, which is not constant, wherein the cap has a reinforced rim above each hole to receive the air/water tube and the irrigation tube, the liner comprising at least one aperture to receive the air/water tube and the irrigation tube.

19. The cap of claim 18, wherein at least one of the holes fits a tubing for insufflation.

20. The cap of claim 18 wherein at least one of the holes fits a gas tube.

21. The cap of claim 18, wherein the cap and the liner are made of the same material.

22. The cap of claim 18, wherein the cap and the liner are made of different material.

23. The cap of claim 18, wherein the cap is made from a plastic material, elastomeric material, thermoplastic material, rigid polymer, or combination thereof.

24. The cap of claim 18, wherein the cap is made of methyl methacrylate acrylonitrile butadiene styrene (MABS), acrylonitrile butadiene styrene (ABS), polyvinyl chloride (PVC), polystyrene, polycarbonate, polypropylene, rubber, nylon, or silicon.

25. The cap of claim 18, wherein the cap and the liner are one contiguous body.

26. The cap of claim 18, wherein the liner comprises a substantially L-shaped cross section.

27. A cap capable of sealing on multiple surfaces comprising: a one-piece liner formed from a single material comprising a top surface that engages an upper wall of the cap and an outer surface being substantially vertically oriented that engages a side wall of said cap, a gap being formed between the upper wall of the cap and the top surface of the liner opposing the upper wall, said side wall extending transversely from said upper wall, and said liner comprising an inclined inner surface to provide a tapered configuration; a thread on said inclined inner surface, wherein the thread is adapted for engaging a variety of bottles; wherein said upper wall comprises at least two openings and said top surface comprises at least one aperture, and one opening of the at least two openings and the at least one aperture receives an irrigation tube and a second opening of the at least two openings receives an air/water tube comprising a water tube and an air tube in a coaxial arrangement, the water tube having a diameter smaller than the air tube and the irrigation tube and the liner has an inner diameter having a tapered configuration, which is not constant, wherein the cap has a reinforced rim above each opening to receive the air/water tube and the irrigation tube, the liner comprising at least one aperture to receive the air/water tube and the irrigation tube.

28. The cap of claim 27 wherein said engaging occurs with no more than two revolutions.

29. A cap comprising an inner surface having positive threads, wherein the threads are adapted for engaging a variety of sterile water containers; a one-piece liner formed from a single material inside said cap capable of sealing on multiple surfaces, said liner comprising a top surface that engages an upper wall of the cap and an outer surface being substantially vertically oriented that engages a side wall of said cap and said liner comprising an inclined inner surface to provide a tapered configuration, said side wall extending transversely from said upper wall, a gap being formed between the upper wall of the cap and the top surface of the liner opposing the upper wall, the inclined inner surface of the liner is configured to engage a variety of bottle necks of varying heights and diameters; and the upper wall comprising two openings and said top surface comprising at least one aperture; one opening and said aperture having a flexible irrigation tubing disposed therein, and a second opening receiving and air/water tube comprising a water tube and an air tube in a coaxial arrangement, the water tube having a diameter smaller than the air tube and the flexible irrigation tubing, and the liner has an inner diameter having a tapered configuration, which is not constant, wherein the cap has a reinforced rim above each opening to receive the air/water tube and the irrigation tube, the liner comprising at least one aperture to receive the air/water tube and the irrigation tube.

30. A cap for sealing a sterile water bottle comprising: a thread on an inner surface providing less than 720° of thread engagement with said sterile water bottle; a one-piece liner formed from a single material inside said cap capable of sealing on multiple surfaces, said liner comprising a top surface that engages an upper wall of the cap and an outer surface being substantially vertically oriented that engages a side wall of said cap, said side wall extending transversely from said upper wall, a gap being formed between the upper wall of the cap and the top surface of the liner opposing the upper wall, and said liner comprising an inclined inner surface to provide a tapered configuration such that the inclined inner surface of the liner is configured to engage a variety of bottle necks of varying heights and diameters, the upper wall comprising at least one hole and the top surface having at least one opening in alignment with the hole, the hole and opening configured to fit an air/water tube and an irrigation tube, wherein the air/water tube comprises a water tube and an air tube in a coaxial arrangement; and at least two sealing surfaces above said thread, and the liner has an inner diameter having a tapered configuration, which is not constant, wherein the cap has a reinforced rim above each opening to receive the air/water tube, the liner comprising at least one aperture to receive the air/water tube and the irrigation tube.

31. The cap of claim 30 further comprising an air filter.

32. The cap of claim 30, wherein the thread has a trapezoid geometry comprising a first base and a second base, wherein the first base is larger than the second base and wherein the first base is adjacent to the wall of the cap.

33. The cap of claim 32, wherein the first base is about 0.090".

34. The cap of claim 32, wherein the second base is about 0.035".

35. The cap of claim 32, wherein the first base is about 0.090" and the second base is about 0.035".

36. The cap of claim 30, wherein the thread comprises a first diameter and a second diameter, wherein the first diameter is larger than the second diameter.

37. The cap of claim 30 wherein the first diameter is about 1.490" and the second diameter is about 1.375".

38. The cap of claim 30, wherein the first diameter is about 1.420" and the second diameter is about 1.300".

39. The cap of claim 30, wherein the thread has a pitch of about 0.16".

40. The cap of claim 30, wherein the thread comprises about 1.75 revolutions.

41. The cap of claim 32, wherein the trapezoidal geometry comprises rounded corners.

42. The cap of claim 30, wherein the inclined inner surface is tapered at an angle of about 2 degrees such that a diameter of a bottom end of the liner is larger than a diameter of a top end of the liner.

43. A cap comprising: a one-piece liner formed from a single material capable of sealing on multiple surfaces, said liner comprising a top surface that engages an upper wall of the cap and an outer surface being substantially vertically oriented that engages a side wall of said cap, said side wall extending transversely from said upper wall, a gap being formed between the upper wall of the cap and the top surface of the liner opposing the upper wall, an inclined inner surface of said liner to provide a tapered configuration to engage a variety of bottle necks of varying heights and diameters; a thread on said inclined inner surface; wherein the upper wall comprises at least one hole fit for an irrigation tube, and an air/water tube and the top surface comprises an opening configured to fit the irrigation tubing, wherein the liner is spaced apart from the opening, and the liner has an inner diameter having a tapered configuration, which is not constant, wherein the cap has a reinforced rim above the opening to receive the irrigation tube, the liner comprising at least one aperture to receive the air/water tube and the irrigation tube.

44. The cap of claim 1, wherein the liner is formed from a single deformable material.

45. The cap of claim 1, wherein the air/water tube and the irrigation tube are secured to the cap by an adhesive material.

46. The cap of claim 1, wherein one of the at least two openings fits a gas tube.

47. The cap of claim 1, wherein the inclined inner surface of the liner comprises decreasing thickness in a direction transverse from the upper wall of the cap.

* * * * *